(12) United States Patent
Saud et al.

(10) Patent No.: US 6,489,493 B2
(45) Date of Patent: Dec. 3, 2002

(54) ACYCLIC CHIRAL DERIVATIVES OF HIBISCUS ACID AND THE PROCESS OF PREPARING THE SAME

(75) Inventors: Ibrahim Ibnu Saud, Kerala (IN); Rani Rajasekharan Nair, Thirnvalla (IN)

(73) Assignee: Department of Science and Technology, Technology Bhavan, New Delhi (IN)

( * ) Notice: Subject to any disclaimer, the term of this patent is extended or adjusted under 35 U.S.C. 154(b) by 0 days.

(21) Appl. No.: 09/946,815

(22) Filed: Sep. 5, 2001

(65) Prior Publication Data

US 2002/0045769 A1 Apr. 18, 2002

(30) Foreign Application Priority Data

Oct. 3, 2000 (IN) .................................. 886/00

(51) Int. Cl.⁷ .................... C07D 317/20; C07D 317/24; C07C 69/675; C07C 69/767
(52) U.S. Cl. .................... 549/453; 549/508; 560/81; 560/98; 560/182
(58) Field of Search ................... 549/453, 508; 560/81, 98, 182

(56) References Cited

U.S. PATENT DOCUMENTS 6,127,553 A * 10/2000 Ibnusaud et al.

* cited by examiner

*Primary Examiner*—Ba K. Trinh
(74) *Attorney, Agent, or Firm*—Sidley Austin Brown & Wood LLP

(57) ABSTRACT

The present invention relates to a novel acyclic chiral derivatives of Hibiscus acid of formula I,

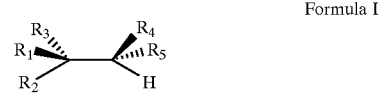

Formula I wherein:

$R_1=R_5$=lower aryl or alkyl ester or substituted aryl or alkyl alcohol $R_3$=substituted aryl or alkyl ester or substituted aryl alcohol $R_2=R_4$=hydroxyl or

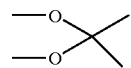

and a process for preparing the same.

23 Claims, No Drawings

ACYCLIC CHIRAL DERIVATIVES OF HIBISCUS ACID AND THE PROCESS OF PREPARING THE SAME

This invention relates to novel acyclic chiral derivatives of hibiscus acid and the process of preparing the same.

BACKGROUND OF THE INVENTION

Hibiscus acid, [(+)-Hydroxycitric acid lactone or (2S,3R)-Tetrahydro-3-hydroxy-5-oxo-2,3-furandicarboxylic acid], can be isolated from the leaves/fruit calyxes of *Hibiscus sabdariffa* or from the leaves of *Hibiscus furcatus*, and *Hibiscus cannabinus*. However the non-availability of Hibiscus acid in the market, in the optically pure form, has resulted in the limited use of Hibiscus acid or its derivatives in the broad area of organic synthesis and pharmaceutical front. In U.S. patent application Ser. No. 09/365,300, the large scale manufacture of Hibiscus acid in the optically pure crystalline form has been described.

During the past two decades there has been a great deal of interest in finding cheap and potential chiral derivatives from chiral pool to accomplish synthetic pathways with a high degree of asymmetric induction.

The object of the present invention is to synthesize novel acyclic chiral derivatives of Hibiscus acid which are found to be important building blocks in organic synthesis and are extensively used for the preparation of optically active ligands and biologically active products.

To achieve the said objective this invention provides a novel acyclic chiral compound of Hibiscus acid of formula I,

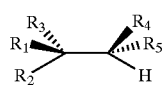

Formula I wherein:
$R_1 = R_5 =$ lower aryl or alkyl ester or substituted aryl or alkyl alcohol
$R_3 =$ substituted aryl or alkyl ester or substituted aryl alcohol
$R_2 = R_4 =$ hydroxyl or

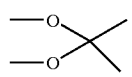

In the above formula I:
$R_1$ & $R_5$ is selected from $-COOCH_3$, $-COOC_2H_5$, $-COOCH(CH_3)_2$, $-C(Ph)_2OH$, $-C(4-MePh)_2OH$, $-C(1-Naphth)_2OH$
$R_2$ and $R_4$ is OH or

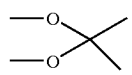

$R_3$ is selected from $-CH_2COOCH_3$, $-CH_2COOC_2H_5$, $-CH_2COOCH(CH_3)_2$, $-CH_2C(Ph)_2OH$, $-CH_2C(4-MePh)_2OH$, $-CH_2C(1-Naphth)_2OH$ to form various chiral derivatives, namely, chiral triesters, chiral ketals, chiral alcohols.

Chiral Triester Derivatives
Ia—$R_1 = R_5 = -COOCH_3$, $R_2 = R_4 = -OH$ and $R_3 = -CH_2COOCH_3$ Ib—$R_1 = R_5 = -COOC_2H_5$, $R_2 = R_4 = -OH$ $R_3 = -CH_2COOC_2H_5$
Ic—$R_1 = R_5 = -COOCH(CH_3)_2$, $R_2 = R_4 32$ $-OH$ and $R_3 = -CH_2COOCH(CH_3)_2$ Chiral Ketal Derivatives
Id—

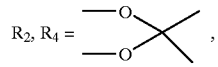

$R_1 = R_5 = -COOCH_3$, $R_3 = -CH_2COOCH_3$
Ie—

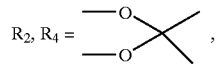

$R_1 = R_5 = -COOC_2H_5$ and $R_3 = -CH_2COOC_2H_5$

Chiral Alcohol Derivatives(diols)
If—

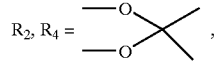

$R_1 = R_5 = -C(Ph)_2OH$ and $R_3 = -CH_2CPh)_2OH$
Ig—

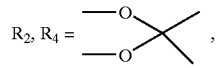

$R_1 = R_5 = -C(4-MePh)_2OH$ and $R_3 = -CH_2C(4-MePh)_2OH$
Ih—

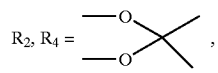

$R_1 = R_5 = -C(1-Naphth)_2OH$ and $R_3 = -CH_2C(1-Naphth)_2OH$

Compound of formula Ia is trimethyl(1S,2R)-1,2-dihydroxy-1,2,3-propanetricarboxylate Compound of formula Ib is Triethyl(1S,2R)-1,2-dihydroxy-1,2,3-propanetricarboxylate.

Compound of formula Ic is Tri isopropyl(1S,2R)-1,2-dihydroxy-1,2,3-propanetricarboxylate.

Compound of formula Id is dimethyl(4S,5R)-2,2-dimethyl-4-(2-oxo-2-methoxyethyl)-1,3-dioxolane-4,5-dicarboxylate (Id)

Compound of formula Ie is diethyl(4S,5R)-2,2-dimethyl-4-(2-oxo-2-ethoxyethyl)-1,3-dioxolane-4,5-dicarboxylate (Ie)

Compound of formula If is (4S,5R)-4-(2-hydroxy-2,2-diphenylethyl)-2,2-dimethyl-alpha,alpha,alpha',alpha'-tetraphenyl-1,3-dioxolane-4,5-dimethanol (If).

The present invention further includes a process for preparing the acyclic chiral triester of formulae Ia–Ic comprising refluxing hibiscus acid with appropriate alcohol in presence of an inorganic catalyst for 6–12 hours, adjusting the pH of the reaction mixture to neutral using aqueous alkali solution, concentrating the said reaction-mixture by evaporation, extracting the said concentrate with an organic solvent, concentrating the said extract to yield the said product.

The said appropriate alcohols are selected from methanol, ethanol and isopropanol.

The said catalyst is conc. HCl and said organic solvent is chloroform.

The present invention also includes a process for preparing the acyclic chiral triester of formulae If–Ih comprising:

adding solution of chiral acetal/ketal in an organic solvent to a solution of appropriate grignard reagent(ArMgX) in an organic solvent, refluxing the mixture for 10–20 hours, adding the inorganic salt solution to the chilled reaction mixture, collecting the organic phase and extracting the aqueous layer further with a suitable organic acid, drying the organic extract using a suitable salt, evaporating the said extract, subjecting the residue to chromatography.

The organic solvent is tetra hydro furan (THF).

The said appropriate grignard reagent is phenyl Mg bromide, methylphenyl Mg bromide, naphthyl Mg bromide.

The said inorganic salt is ammonium chloride.

The said organic solvent used for extraction is ether.

The said salt used for drying the extract is sodium sulphate.

The chromatography employed for purification is column chromatography. The gel used for chromatography is silica gel. The eluant used for chromatography is hexane chloroform mixture.

Summary of the chiral derivatives of Hibiscus acid is given below in scheme I:

Scheme I

1*/8

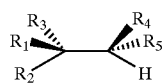

Ia: $R_1=R_5=$—$COOCH_3$; $R_2=R_4=$—$OH$; $R_3=$—$CH_2COOCH_3$

Ib: $R_1=R_3=$—$COOC_2H_5$; $R_2=R=$—$OH$; $R_3=$—$CH_2COOCH_5$

Ic: $R_1=R_5=$—$COOCH(CH_3)_2$; $R_2=R_4=$—$OH$; $R_3=$—$CH_2COOCH(CH_3)_2$

Id:

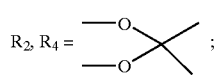

$R_1=R_5=$—$COOCH_3$; $R_3=$—$CH_2COOCH_3$

Ie:

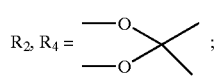

$R_1=R_5=$—$COOC_2H_5$; $R_3=$—$CH_2COOC_2H_5$

If:

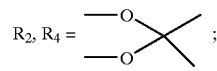

$R_1R_5=$—$C(Ph)_2OH$; $R_3=$—$CH_2C(Ph)_2OH$

Ig:

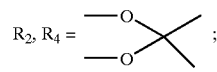

$R_1=R_5=$—$C(4MePh)_2OH$; $R_3=$—$CH_2C(4-MePh)_2OH$

Ih:

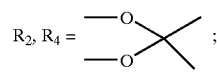

$R_1=R_5=$—$C(1-Naphth)_2OH$; $R_3=$—$CH_2C(1-Naphth)_2OH$

Standard procedures are followed for the preparation of various chiral ketals of the type Id and Ie.

The invention will now be described with reference to the foregoing examples:

EXAMPLE 1

Trimethyl(1S,2R)-1,2-dihydroxy-1,2,3-propanetricarboxylate (Ia)

Hibiscus acid (1.0 g, 5 mmol) was refluxed with methanol (10 ml) and conc. HCl (0.4 ml) for 12 hours. pH of the reaction mixture was adjusted to neutral using aqueous solution of sodium bicarbonate. The resultant solution was evaporated and extracted with chloroform (4×20 ml). The combined chloroform extracts was dried (sodium sulphate) and on concentration furnished Ia.

Yield: 0.5 g (38%).

EXAMPLE 2

Triethyl(1S,2R)-1,2-dihydroxy-1,2,3-propanetricarboxylate (Ib)

Ib was prepared from Hibiscus acid and ethanol in 39% yield by the same procedure used to prepare Ia from Hibiscus acid.

EXAMPLE 3

Triisopropyl(1S,2R)-1,2-dihydroxy-1,2,3-propanetricarboxylate (Ic)

Ic was prepared from Hibiscus acid and dry isopropanol by the same procedure used to prepare Ia from Hibiscus acid Melting point: 110° C.

Yield: 4.0 g (66%)).

EXAMPLE 4

Dimethyl(4R,5S)-2,2-dimethyl-4-(2-oxo-2-methoxyethyl)-1,3-dioxolane-4,5-dicarboxylate (Id)

To Ia (1.0 g, 4 mmol) in dry acetone (25 ml), anhydrous copper sulphate (1.0 g) and a few drops of conc. sulphuric acid were added. The mixture was refluxed for four hours, followed by filtration and neutralisation using aqueous sodium bicarbonate solution. The resultant solution obtained after evaporation was extracted with hexane (4×20 ml). The combined extracts after washing with water (50 ml) was dried with sodium sulphate. Upon evaporation, Id obtained as an yellow oil.

Yield: 0.4 g (35%).

EXAMPLE 5

Diethyl(4R,5S)-2,2-dimethyl4-(2-oxo-2-ethoxyethyl)-1,3-dioxolane-4,5-dicarboxylate (Ie)

Ie was prepared from Ib in 53% yield by the same procedure used to prepare Id from Ia.

EXAMPLE 6

(4R,5S)-4-(2-hydroxy-2,2-diphenylethyl)-2,2-dimethyl-alpha,alpha,alpha',alpha'-tetraphenyl-1,3-dioxolane-4,5-dimethanol A solution of Id (0.5 g, 1.7 mmol, in 5 ml THF) was added to a solution of Phenyl magnesium bromide in THF (10 ml, 1M) and the mixture was refluxed for 15 hours. To the chilled reaction mixture aqueous ammonium chloride solution (20 ml) was added. The organic phase was collected and the aqueous layer was extracted with ether (5×10 ml). The organic phase and the ether extracts were combined and dried (sodium sulphate). The solution upon evaporation followed by column chromatography (silica gel 60–120 mesh, eluent: hexane) yielded If.

Yield: 0.5 g (44%).

USES

Pharmaceutical applications.

Chiral derivatives Ia–Ic and If–Ih is used for the preparation of chiral catalyst and chiral auxiliaries.

the derivatives of Ia–Ih is used as chiral synthons.

We claim:

1. A novel acyclic chiral compound of Hibiscus acid of formula I,

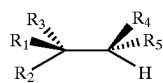

Formula I wherein:

$R_1 = R_5$ = lower aryl or alkyl ester or substituted aryl or alkyl alcohol $R_3$ = substituted aryl or alkyl ester or substituted aryl alcohol $R_2 = R_4$ = hydroxyl or

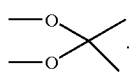

2. A compound as claimed in claim 1 wherein, $R_1$ & $R_5$ is selected from —OOCH$_3$, —COOC$_2$H$_5$, —COOCH(CH$_3$)$_2$, —C(Ph)$_2$OH, —C(4-MePh)$_2$OH, —C(1-Naphth)$_2$OH $R_2$ and $R_4$ is OH or

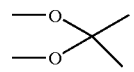

$R_3$ is selected from —CH$_2$COOCH$_3$, —CH$_2$COOC$_2$H$_5$, —CH$_2$COOCH(CH$_3$)$_2$, —CH$_2$C(Ph)$_2$OH, —CH$_2$C(4-MePh)$_2$OH, —CH$_2$C(1-Naphth)$_2$OH.

3. A compound as claimed in claim 2 wherein, $R_1=R_5$=—COOCH$_3$, $R_2=R_4$=—OH and $R_3$=—CH$_2$COOCH$_3$ and said compound is trimethyl(1S,2R)-1,2-dihydroxy-1,2,3-propanetricarboxylate

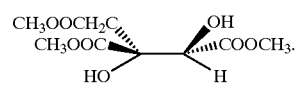

4. A compound as claimed in claim 2 wherein $R_1=R_5$=—COOC$_2$H$_5$, $R_2=R_4$=—OH $R_3$=—CH$_2$COOC$_2$H$_5$ and said compound is Triethyl(1S,2R)-1,2-dihydroxy-1,2,3-propanetricarboxylate,

5. A compound as claimed in claim 2 wherein $R_1=R_5$=—COOCH(CH$_3$)$_2$, $R_2=R_4$=—OH and $R_3$=—CH$_2$COOCH(CH$_3$)$_2$ and said compound is Tri isopropyl(1S,2R)-1,2,3-dihydroxy-1,2,3-propanetricarboxylate,

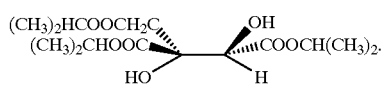

6. A compound as claimed in claim 2 wherein $R_2$,

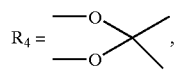

$R_1=R_5$=—COOCH$_3$, $R_3$=—CH$_2$COOCH$_3$ $_2$ and said compound is dimethyl(4S,5R)-2,2-dimethyl-4-(2-oxo-2-methoxyethyl)-1,3-dioxolane-4,5-dicarboxylate,

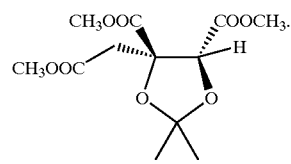

7. A compound as claimed in claim 2 wherein $R_2$,

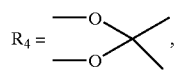

$R_1=R_5$=—COOC$_2$H$_5$ and $R_3$=—CH$_2$COOC$_2$H$_5$ and said compound is diethyl (4S,5R)-2,2-dimethyl-4-(2-oxo-2-ethoxyethyl)-1,3-dioxolane-4,5-dicarboxylate,

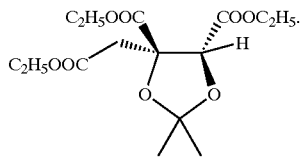

8. A compound as claimed in claim 2 wherein $R_2$,

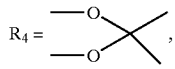

$R_1=R_5=$—C(Ph)$_2$OH and $R_3=$—CH$_2$C(Ph)$_2$ OH and said compound is (4S,5R)-4-(2-hydroxy-2,2-diphenylethyl)-2,2-dimethyl-alpha,alpha,alpha',alpha'-tetraphenyl-1,3-dioxolane-4,5-dimethanol

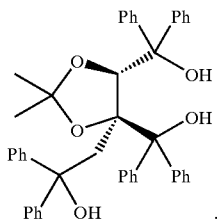

9. A compound as claimed in claim 2 wherein $R_2$,

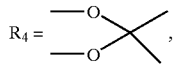

$R_1=R_5=$—C(4-MePh)$_2$OH and $R_3=$—CH$_2$C(4-MePh)$_2$OH and said compound is

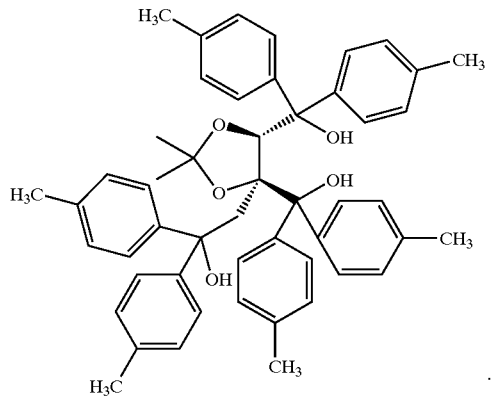

10. A compound as claimed in claim 2 wherein $R_2$,

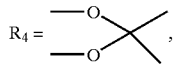

$R_1=R_5=$—C(1-Naphth)$_2$OH and $R_3=$—CH$_2$C(1-Naphth)$_2$OH and said compound is

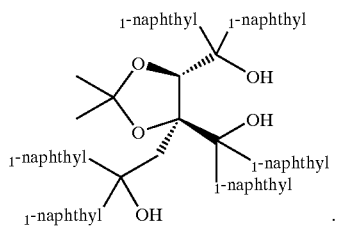

11. A process for preparing the acyclic chiral triester of formulae Ia–Ic of as claimed in claim 1 comprising
refluxing hibiscus acid with appropriate alcohol in presence of an inorganic catalyst for 6–12 hours,
adjusting the pH of the reaction mixture to neutral using aqueous alkali solution,
concentrating the said reaction-mixture by evaporation,
extracting the said concentrate with an organic solvent,
concentrating the said extract to yield the said product.

12. A process as claimed in claim 11 wherein, the said appropriate alcohols are selected from methanol, ethanol and isopropanol.

13. A process as claimed in claim 11 wherein, the said catalyst is conc. HCl.

14. A process as claimed in claim 11 wherein, the said organic solvent is chloroform.

15. A process for preparing compounds of formulae If–Ih as claimed in claim 1 comprising:
adding solution of compounds of formulae Id–Ie (chiral ketal) in an organic solvent to a solution of appropriate grignard reagent (ArMgX) in an organic solvent,
refluxing the mixture for 10–20 hours,
adding the inorganic salt solution to the chilled reaction mixture,
collecting the organic phase and extracting the aqueous layer further with a suitable organic acid,
drying the organic extract using a suitable salt,
evaporating the said extract,
subjecting the residue to chromatography.

16. A process as claimed in claim 15 wherein, the organic solvent is tetra hydro furan (ITIF).

17. A process as claimed in claim 15 wherein, the said appropriate grignard reagent is phenyl Mg bromide, methylphenyl Mg bromide, naphthyl Mg bromide.

18. A process as claimed in claim 15 wherein, the said inorganic salt is ammonium chloride.

19. A process as claimed in claim 15 wherein, the said organic solvent used for extraction is ether.

20. A process as claimed in claim 15 wherein, the said salt used for drying the extract is sodium sulphate.

21. A process as claimed in claim 15 wherein, the chromatography employed for purification is column chromatography.

22. A process as claimed in claim 21 wherein, the gel used for chromatography is silica gel.

23. A process as claimed in claim 22 wherein, the element used for chromatography is hexane chloroform mixture.

* * * * *